United States Patent
Young et al.

(10) Patent No.: US 7,322,354 B2
(45) Date of Patent: Jan. 29, 2008

(54) BREATH ACTUATED DRY POWDER INHALER AND TAPE DOSE STRIP

(75) Inventors: Matthew Young, Barkway (GB); Stuart Kay, Barkway (GB); Neil Harrison, Sutton Coldfield (GB); Ian Darby, Ruddington (GB); Peter Crew, Ruddington (GB); Anne Powell, Ruddington (GB); Cheryl Vanessa Rogerson, Ruddington (GB)

(73) Assignee: Valois S.A.S, Le Neubourg (FR)

( * ) Notice: Subject to any disclaimer, the term of this patent is extended or adjusted under 35 U.S.C. 154(b) by 68 days.

(21) Appl. No.: 10/984,870

(22) Filed: Nov. 10, 2004

(65) Prior Publication Data

US 2005/0081853 A1    Apr. 21, 2005

Related U.S. Application Data

(60) Division of application No. 10/350,154, filed on Jan. 22, 2003, now Pat. No. 7,171,965, which is a continuation-in-part of application No. 10/099,592, filed on Mar. 15, 2002, now Pat. No. 7,069,929, which is a continuation-in-part of application No. 09/773,261, filed on Jan. 31, 2001, now Pat. No. 6,715,486, which is a continuation-in-part of application No. 09/495,494, filed on Feb. 1, 2000, now Pat. No. 6,427,688.

(51) Int. Cl.
*A61M 5/00* (2006.01)

(52) U.S. Cl. ............................ 128/203.15; 128/203.21; 128/203.12; 604/58

(58) Field of Classification Search .......... 128/203.15, 128/203.21, 604, 58, 203.12, 103.19, 203.19, 128/200.14, 200.21, 200.23, 200.12; 604/58; 222/94, 103, 160, 541.1
See application file for complete search history.

(56) References Cited

U.S. PATENT DOCUMENTS

| 3,630,346 | A |   | 12/1971 | Burnside |           |
|-----------|---|---|---------|----------|-----------|
| 5,524,765 | A |   | 6/1996  | Gutentag |           |
| 5,544,646 | A |   | 8/1996  | Lloyd et al. |       |
| 5,590,645 | A | * | 1/1997  | Davies et al. | 128/203.15 |
| 5,619,984 | A | * | 4/1997  | Hodson et al. | 128/203.15 |
| 5,622,166 | A |   | 4/1997  | Eisele et al. |       |
| 5,727,687 | A |   | 3/1998  | Renner |             |

(Continued)

FOREIGN PATENT DOCUMENTS

WO    WO 9606581 A1    3/1996

(Continued)

*Primary Examiner*—Justine R. Yu
*Assistant Examiner*—Shumaya B. Ali
(74) *Attorney, Agent, or Firm*—Sughrue Mion, Pllc.

(57) ABSTRACT

A method for operating a dry powder inhaler, the dry powder inhaler having a dose tape having spaced apart doses of a powder pharmaceutical, each dose being in a respective sealed blister. The inhaler includes a breath actuated blister opening system that sequentially opens a blister on the tape. The method involves routing the dose tape between first and second rotating elements; spring biasing the first rotating element to turn in a first direction; holding the first rotating element from rotating against the spring biasing; and releasing the first rotating element, and allowing it to rotate a fraction of one rotation, when air flows adjacent to the first rotating element.

14 Claims, 12 Drawing Sheets

U.S. PATENT DOCUMENTS

| | | |
|---|---|---|
| 5,873,360 A | 2/1999 | Davies et al. |
| 6,182,655 B1 | 2/2001 | Keller et al. |
| 6,378,519 B1 | 4/2002 | Davies et al. |
| 6,425,888 B1 | 7/2002 | Embleton et al. |
| 6,427,688 B1 | 8/2002 | Ligotke et al. |
| 6,726,665 B1 | 4/2004 | Embleton et al. |
| 6,752,148 B1 | 6/2004 | McGinn et al. |
| 6,880,555 B1 | 4/2005 | Brunnberg et al. |
| 2005/0081851 A1 | 4/2005 | Young et al. |
| 2005/0087188 A1 | 4/2005 | Young et al. |

FOREIGN PATENT DOCUMENTS

| | | |
|---|---|---|
| WO | WO 9944663 A1 | 9/1999 |

* cited by examiner

BREATH ACTUATED DRY POWDER INHALER AND TAPE DOSE STRIP

This is a divisional of U.S. patent application Ser. No. 10/350,154, filed Jan. 22, 2003 now U.S. Pat. No. 7,171,965, which is a continuation-in-part of U.S. patent application Ser. No. 10/099,592, filed Mar. 15, 2002 and now U.S. Pat. No. 7,069,929, which is a continuation-in-part of U.S. patent application Ser. No. 09/773,261, filed Jan. 31, 2001 and now U.S. Pat. No. 6,715,486 B2, which is a continuation-in-part of U.S. patent application Ser. No. 09/495,494, filed Feb. 1, 2000 now U.S. Pat. No. 6,427,688 B1, with each of these applications incorporated herein by reference.

BACKGROUND OF THE INVENTION

The field of the invention is dry powder inhalers.

Inhalers are used to deliver drugs into a patient's lungs. Typically, an inhaler contains or provides a mixture of drug particles and air or propellant gas. The mixture is delivered by the patient inhaling from a mouthpiece on the inhaler with the air or propellant gas carrying the drug particles into the patient's lungs.

In dry powder inhalers, the drug particles, in the form of a fine dry powder, are entrained into an airflow and inhaled by the patient. Dry powder inhalers are often used for treating bronchial asthma. However, drugs delivered via a dry powder inhaler can also be used to treat many conditions, including conditions unrelated to the lung, via the systemic absorption of the drug into the bloodstream, through the lung.

Treatment of certain conditions, such as asthma, requires a frequent dosing regimen, with the patient taking e.g., two doses each day. Accordingly, a dry powder inhaler able to deliver a large number of doses, such as 60, 90, or even 120 doses, before the inhaler needs to be refilled or replaced, would be advantageous. Some proposed dry powder inhalers achieve the goal of providing large numbers of doses by individually metering out one dose at a time from a bulk powder storage compartment within the inhaler. However, with these designs, it is difficult or impossible to seal water vapor out of the bulk powder. Consequently, powder caking or clumping or particle size growth may result, affecting how well the powder is disbursed in air. This tends to decrease the dose actually provided to the patient and/or lead to inconsistent doses.

To avoid this disadvantage while still providing a large number of doses, dry powder inhalers using a dose tape or strip have been used. The flexible strip has spaced apart pockets each containing a dose of pharmaceutical powder. By winding the strip into a coil, a large number of doses may be contained within a compact inhaler. The doses are sequentially released by incrementally peeling apart top and bottom layers of the strip or tape. While these types of dose strip or tape inhalers can provide a large number of doses, while also better maintaining the physical stability of the powder by sealing out water vapor, disadvantages remain. For example, it can be difficult to avoid double dosing with these types of inhalers, i.e., opening two or more of the pockets or containers on the dose tape before inhaling, causing the patient to inhale a much larger dose than intended. In addition, since known dose tape inhalers unseal each dose of the tape via mechanical actuation by the patient, a dose can be released or unsealed from the tape and exposed to water vapor in the environment unless the dose is promptly inhaled. In addition, certain known dose strip inhalers have relatively complex mechanical designs, adding to manufacturing complexity and cost.

Accordingly, there is a need for an improved dry powder dose tape inhaler.

SUMMARY OF THE INVENTION

In a first aspect of the invention, a blister or dose tape for use in an inhaler has blisters or containers formed in a formpack layer. A lidstock layer is attached to the formpack layer sealing a dose of dry powder pharmaceutical within each of the blisters. A tear strip is attached to the lidstock layer over each of the blisters, preferably with a locally applied adhesive. The lidstock layer is advantageously permanently attached to the formpack layer. In use, the tape is separable into a first strip section including the formpack layer and the lidstock layer areas surrounding the blisters, and a second strip section including the tear strip and spaced apart disks of the lidstock attached to the tear strip. As the tear strip is pulled away from the formpack layer, the disk-shaped areas of the lidstock at each blister are sheared out of the lid layer and remain with the tear strip. The blisters advantageously hold a dry powder or a liquid.

In a second aspect of the invention, the blister tape is used in a dry powder inhaler having a powder dispersion engine including beads movable within a dispersion chamber. A blister opening system within the inhaler sequentially opens blisters on the tape, releasing the powder contents of each blister into an airflow path leading into the dispersion chamber.

In a third aspect, the blister opening system is breath actuated. When a patient or user inhales on a mouthpiece of the inhaler connecting with an airflow path, the blister opening system automatically opens a blister. Additional blisters cannot be opened without resetting the inhaler and again inhaling on the mouthpiece. Accordingly, the potential for inadvertently providing multiple doses (in a single inhalation) is reduced.

In a fourth aspect, the blister opening system includes first and second rotating elements. A spring biases the first rotating element to turn in a first direction. A breath trigger holds the first element against rotation until the trigger is released, by inhaling on a mouthpiece of the inhaler. Biasing of the first rotating element is preferably achieved by tensioning a spring by pivoting a mouthpiece dust cover.

In a fifth aspect, the blister opening system exerts force only on a tear or pull strip of the tape. This avoids potential damage to the other layers or strips of the tape that actually form the seal around the dose.

In a sixth aspect, the layers or strips that seal the dose are free of holes or openings used by the blister opening system for advancing the tape. This provides for a compact tape design.

The invention resides as well in subsystems, components, and steps as described below.

It is an object of the invention to provide an improved dose tape dry powder inhaler.

BRIEF DESCRIPTION OF THE DRAWINGS

In the drawings, wherein the same reference number indicates the same element, in each of the views.

DETAILED OF DESCRIPTION OF THE DRAWINGS

Figure 1:
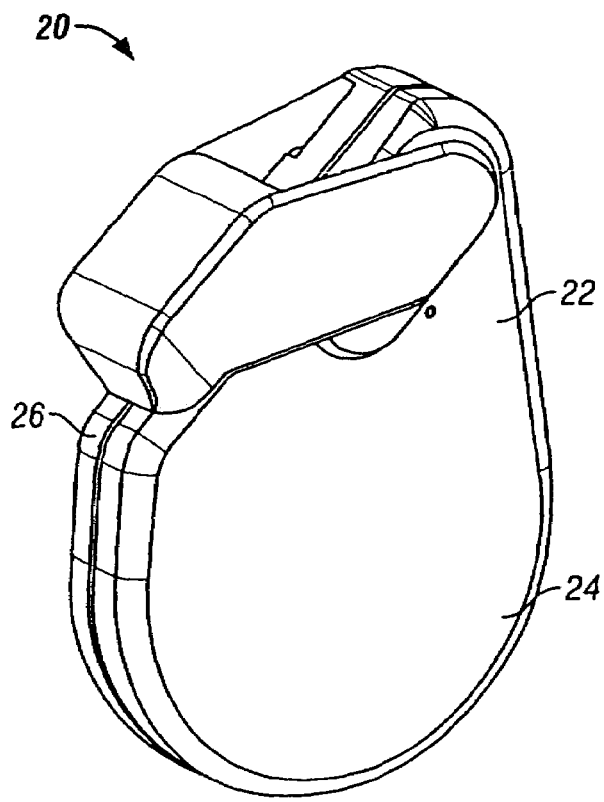
FIG. 1 is a top and front perspective view of the present inhaler, with the dustcap in the closed position.
Figure 2:
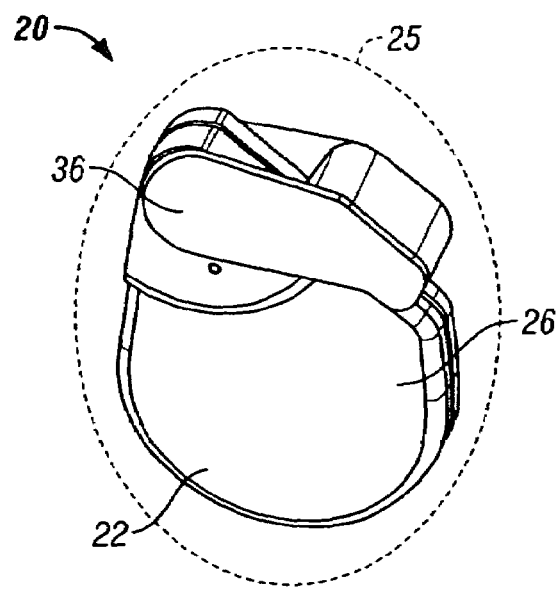
FIG. 2 is a bottom and front perspective view of the inhaler shown in FIG. 1.
Figure 3:
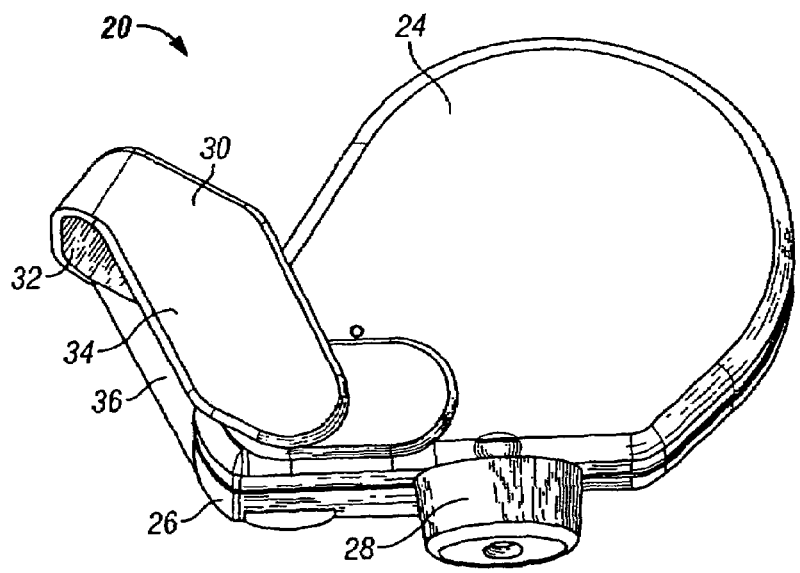
FIG. 3 is a top and front perspective view of the inhaler of FIG. 1 with the dustcap in the open position.

Turning now to the drawings, as shown in FIGS. 1, 2, and 3, an inhaler 20 has an inhaler housing 22 formed by a top housing 24 and bottom housing 26. A dustcap 30 is pivotable from a closed position, as shown in FIG. 1, to an open position, as shown in FIG. 3. In the closed position, a cup section 32 of the dustcap 30 supported by an upper arm 34 and a lower arm 36 covers the mouthpiece 28.

Figure 4:
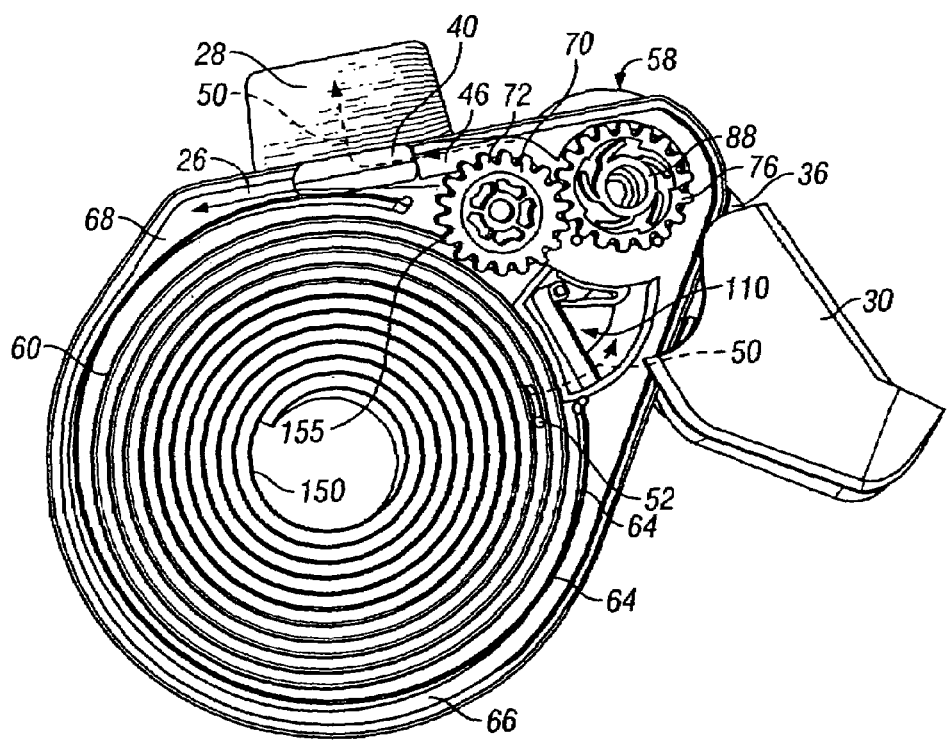
FIG. 4 is a top perspective view of the inhaler of FIG. 3 with the top housing removed for purpose of illustration.

Turning to FIG. 4, the inhaler 20 includes an airflow path generally designated by dotted lines at 50. The airflow path extends from an inlet 52 in the housing 22 past or through a dose tape advancing/opening subsystem 58, into a dispersion chamber 40 and out through the mouthpiece 28. The dispersion chamber 40 has an annular open space in which one or more beads move, as described in International Application PCT/US01/03248 (corresponding to U.S. patent application Ser. No. 09/773,261) incorporated herein by reference.

Referring still to FIG. 4, a dose or blister tape or strip 150 is formed into a spool 60 within the inhaler 20. A tape retainer wall 64 surrounds the spool 60, except at the tape advance/opening system 58.

Figure 5:
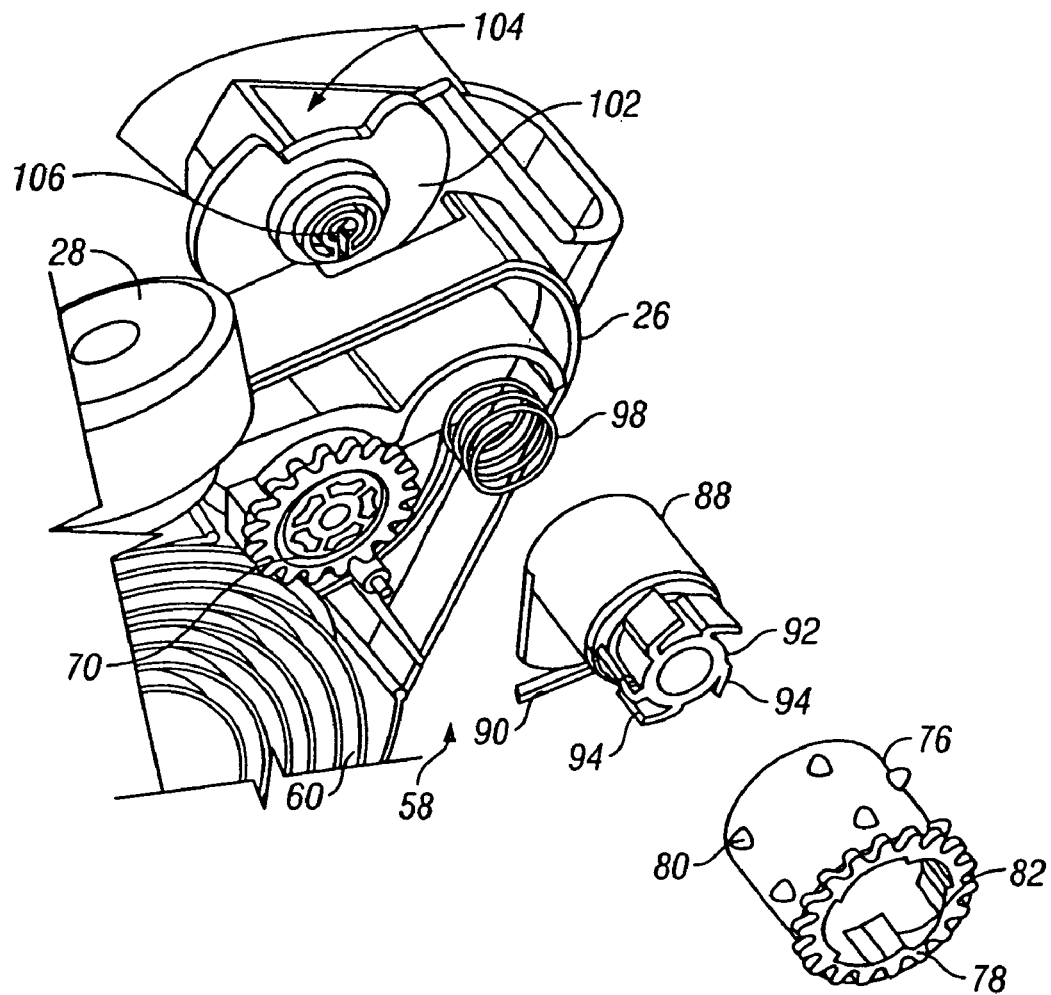
FIG. 5 is an exploded view fragment showing elements of the blister opening system of FIG. 4.
Figure 6:
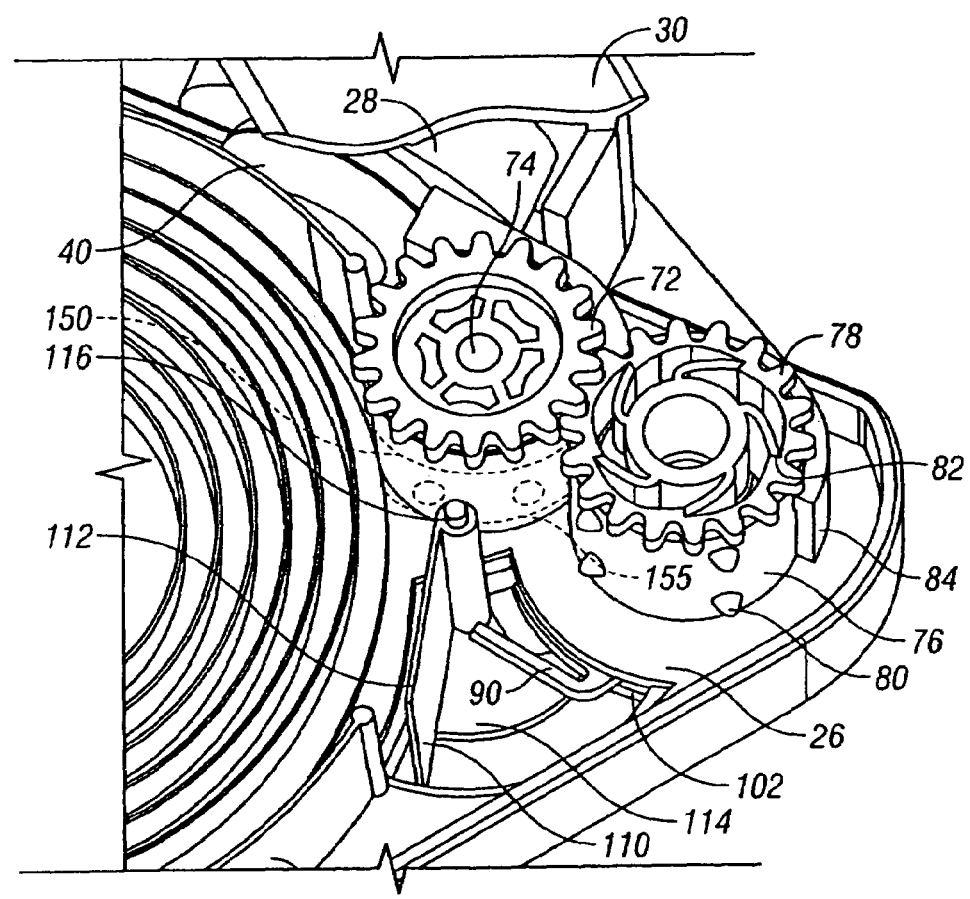
FIG. 6 is a top perspective view of the blister opening system shown in FIG. 5, in the initial or closed position.

Referring to FIGS. 4, 5, and 6, the tape advance/opening system 58 includes a breath flap assembly 110 having a breath wall 112 and a bottom plate 114 joined together or integral with a pivot post 116 pivotably supported on the bottom housing 26.

Figure 10:
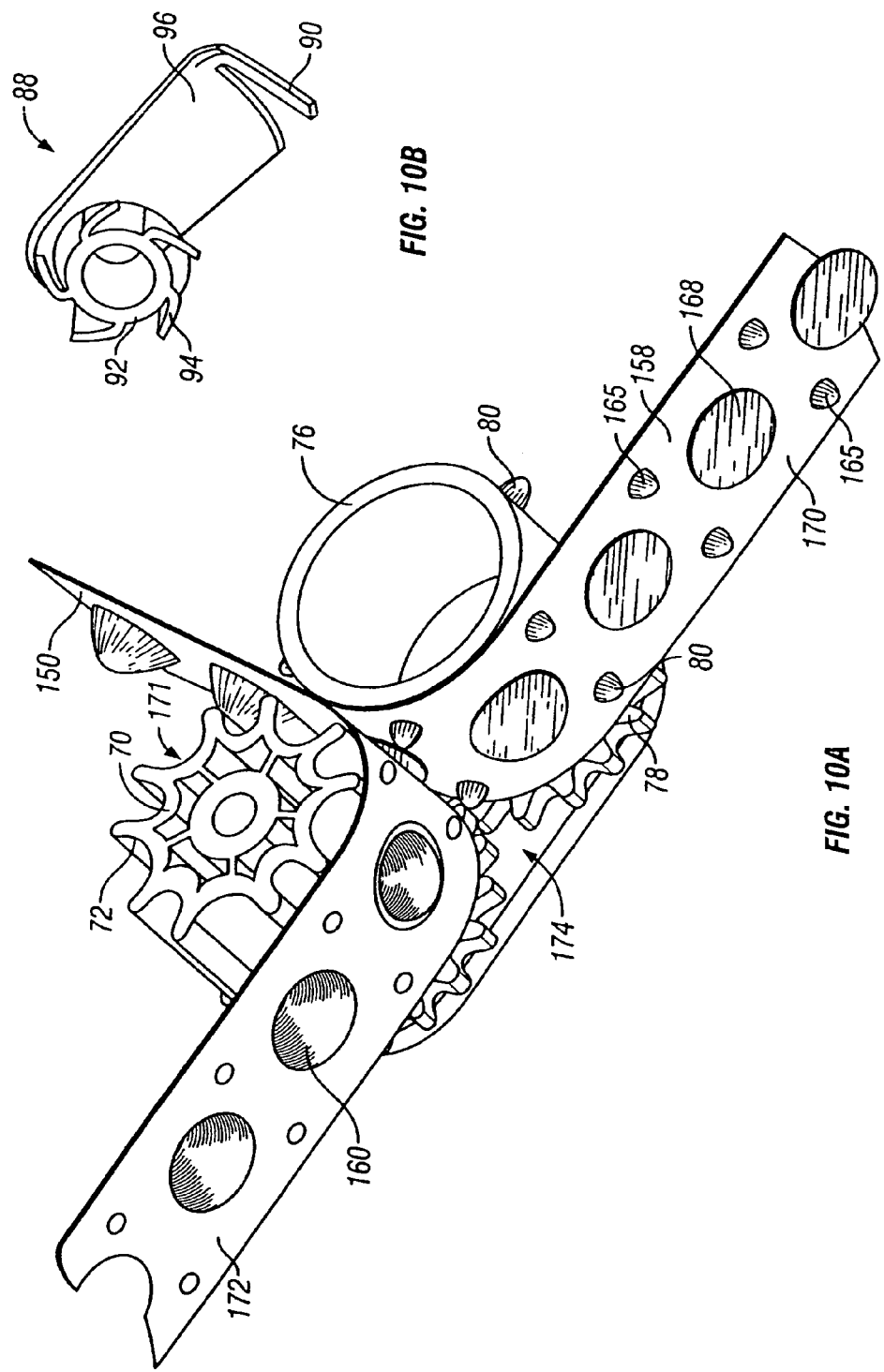
FIG. 10A is a bottom perspective view of components of the blister opening system shown in FIG. 4.
FIG. 10B is a perspective view of the ratchet shown in FIGS. 4 and 5.

Referring to FIGS. 5 and 10B, the tape advance/opening system 58 includes a ratchet 88 having a trigger arm 90 and a ratchet head 92 attached to a trigger plate 96. Resilient or flexible ratchet arms 94 spiral outwardly from the ratchet head 92. Referring to FIG. 5, a drive spool 76 has a spur gear 78 at its top end. Tape pins 80 extend radially outwardly from the cylindrical body of the drive spool 76 below the spur gear 78. Ratchet teeth 82 are provided on the inside upper end of the drive spool 76, within the perimeter of the spur gear 78. The drive spool 76 is positioned over and around the ratchet 88, with the ratchet arms 94 engagable into the ratchet teeth 82, allowing the ratchet 88 to drive the drive spool 76 in a forward (clockwise in FIG. 4) direction, but not in the reverse direction.

Referring still to FIG. 5, the lower dustcap arm 36 is joined (bonded, pinned, sonically welded, etc.) to a loading cam 102 having a central cam hub 106 and a cam recess 104. A spring 98 is secured in the cam hub 106 and to the ratchet 88. As shown in FIG. 6, a capstan 70 pivotably supported on a mounting post 74 extending up from the bottom housing 26 has a spur gear 72 at its top end which meshes with the spur gear 78 of the drive spool 76. The leading end 155 of the tape spool 60 extends around the cylindrical body of the capstan 70, as it moves into the tape advance/opening system 58.

Figure 11:
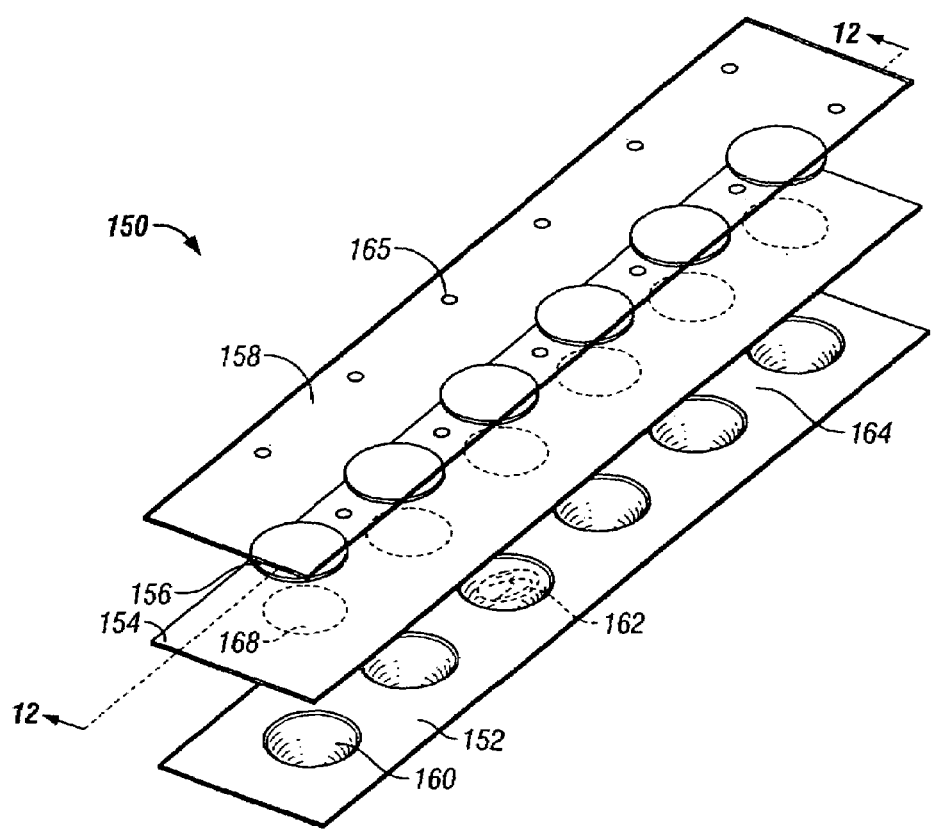
FIG. 11 is an exploded perspective view of the blister tape shown in FIGS. 4 and 10A.
Figure 12:
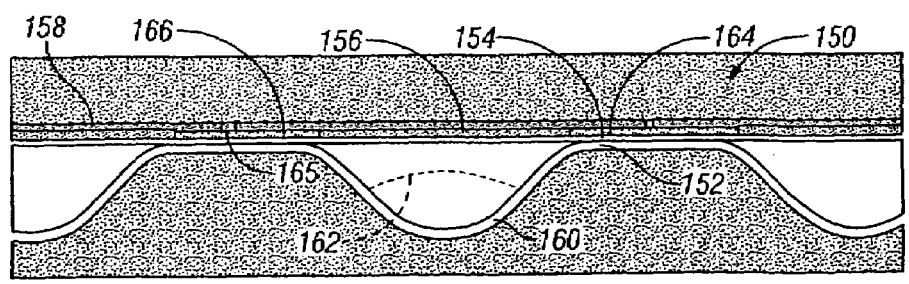
FIG. 12 is a section view taken along line 12-12 of FIG. 11.
Figure 13:
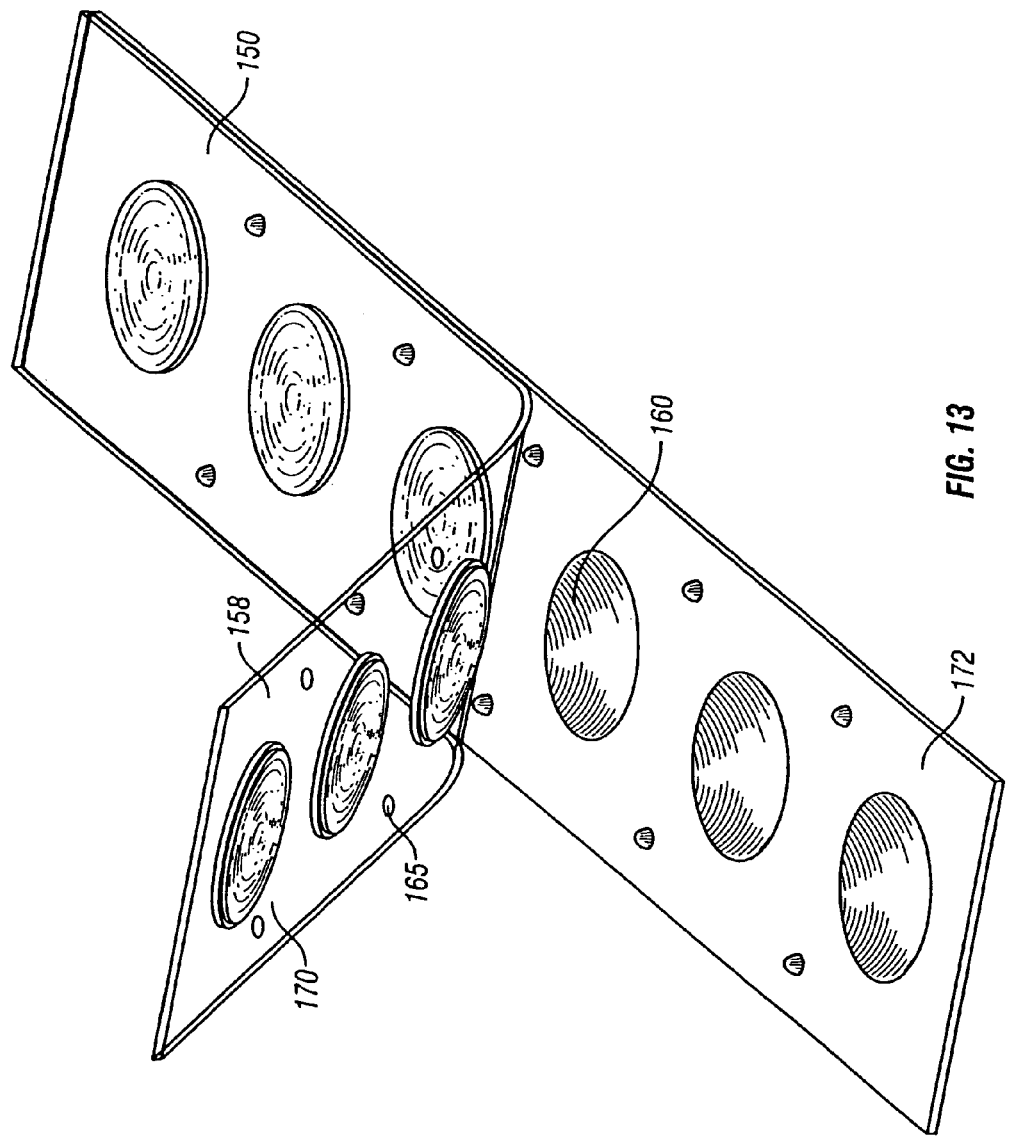
FIG. 13 is a perspective view showing the tape of FIG. 12 after use and separated into a formpack/sheared lidstock layer, and a tear strip/lidstock disk layer.

Referring now to FIGS. 11, 12, and 13, the dose tape 150 has a formpack strip or layer 152 with equally linearly spaced apart recesses, containers, or blisters 160. The formpack layer 152 is preferably a metal foil, such as aluminum, with the blisters 160 formed in the formpack 152 using well-known techniques. A measured volume of pharmaceutical powder 162 is placed into each blister 160. A lidstock strip or layer 154, preferably also a metal foil, such as aluminum, is preferably permanently attached to the formpack layer 152, using well-known techniques, such as compression welding, adhesives, etc. See for example, U.S. Pat. Nos. 4,778,054 and 6,029,663, incorporated herein by reference. The areas of the lidstock layer 154 directly over the blisters 160 do not contact the formpack layer 152 and are not attached, bonded, welded, etc. to the formpack layer 152. Rather, these areas, referred to as lidstock disks 168, and shown in dotted lines in FIG. 11, are suspended over the blisters 160.

A shear or tear strip or layer 158 is attached to each of the lidstock disks 168, preferably using a locally applied adhesive 156. However, other attachment techniques may also be used. The tear strip 158 is advantageously Mylar. The tear strip includes pairs of drive holes between the blisters.

Referring to FIG. 12, the locally applied adhesive 156, if used, is placed over the lidstock disks 168. In the land areas 164 in-between adjacent blisters 160, the tear strip 158 is preferably suspended above the lidstock layer 154, leaving a gap or space 166 between the tear strip 158 and lidstock layer 154 between th blisters 160.

Referring momentarily to FIG. 13, the dose tape 150 is manufactured so that when the tear strip 158 is pulled away from the formpack strip, the lidstock disks 168 shear out of the lidstock strip 154, to unseal the blisters 160. After use, the dose tape 150 is separated into a used lid strip 170 including the tear strip 158, adhesive 156 (if used), and lidstock disks 168, and a used formpack strip 172 including the formpack layer or strip 152 and the areas of the lidstock layer 154 surrounding the blisters 160.

In use, the inhaler 20 is removed from its overwrap or package 25. The dustcap 30 is in the closed position as shown in FIGS. 1 and 2. While preferably holding the inhaler in an upright position, with the housing top 24 facing up, the user pulls the dustcap 30 away from the mouthpiece 30, to the open position shown in FIG. 3. This movement advances the tape 150 and opens a blister or container 160 on the tape, in the following sequence.

The inhaler 20 is provided with the leading end 155 of the spool 60 of the tape 150 engaged between the capstan 70 and the drive spool 76. Specifically, at least one, and preferably two pairs of the tape pins 80 extend through the drive holes 165 in the tear strip positioned in-between the blisters 160. No drive holes are provided in the formpack and lidstock layers. As shown in FIG. 6, in the closed position, the dustcap 30 covers over the mouthpiece 28. This helps to keep the mouthpiece 28 clean between uses.

Figure 7:
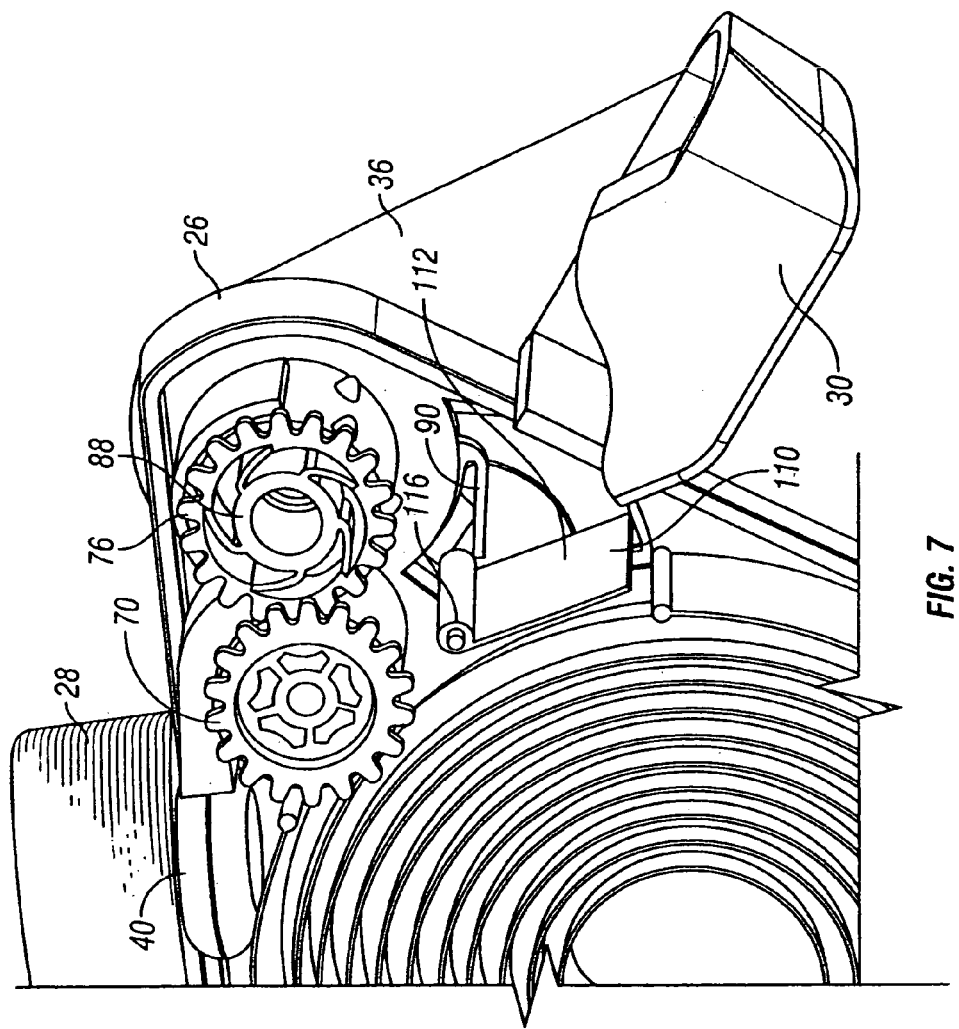
FIG. 7 is a top perspective view thereof with the inhaler in the open/ready position.

Moving to FIG. 7, the user pivots the dustcap 30 from the closed position shown in FIG. 6, to the open position shown in FIG. 7. The loading cam 102 moves with the dustcap 30, as it is secured to the lower arm 36 of the dustcap 30. This movement (of about 130 degrees in the embodiment shown) tensions the spring 98, which in turn biases the ratchet 88 in a forward direction (clockwise in FIG. 7). The inhaler may alternatively be designed so that a spring is tensioned by moving the dustcap from an open position to a closed position. The recess 104 in the cam moves into alignment with or adjacent to the bottom plate 114 of the breath flap assembly 110. The ratchet arms 94 which flex outwardly, engage against the ratchet teeth 82 on the inside surface of the drive spool 76. However, the ratchet 88 and drive spool 76 cannot turn, because the trigger arm 90 of the ratchet 88 is held against the breath flap assembly 110. Specifically, the end of the trigger arm 90 presses against the pivot post 116 and breath wall 112. This holds the ratchet 88 and drive spool 76 against rotation. Referring to FIGS. 6 and 7, accordingly the opening movement of the dustcap 30 only tensions the spring 98, without (significantly) moving any of the other components of the tape advance/opening system 58.

Figure 8:
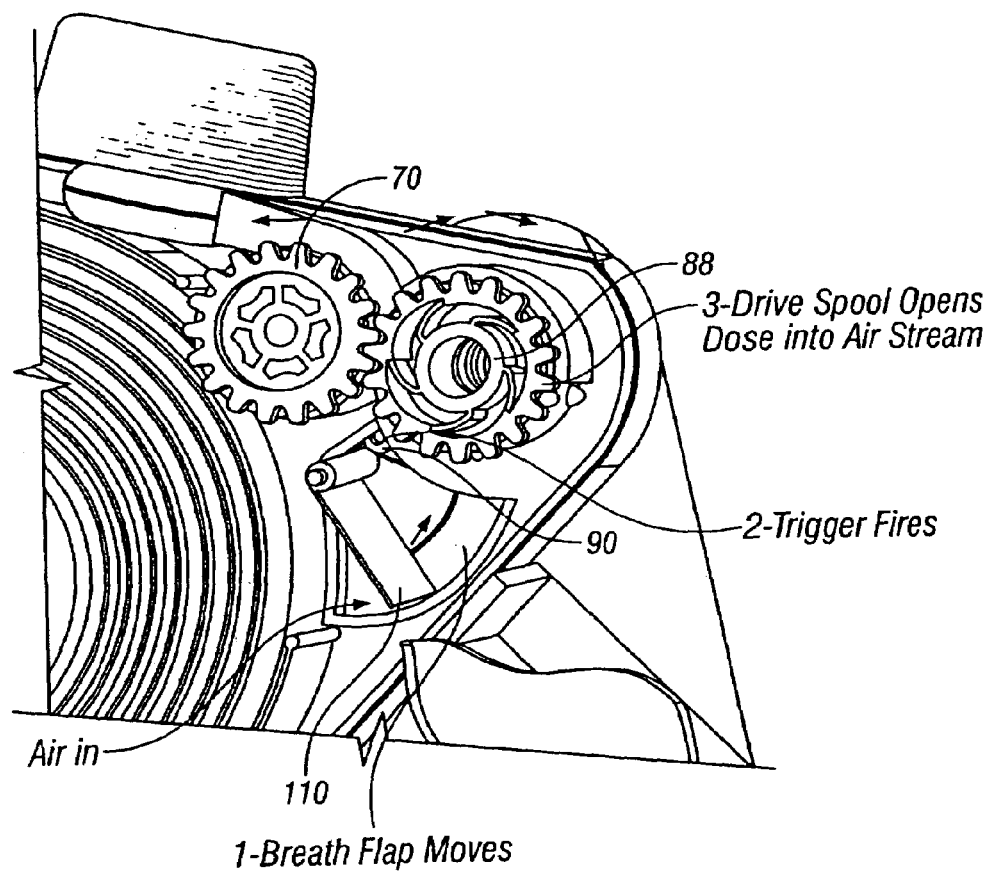
FIG. 8 is a top perspective view thereof showing the inhaler during inhalation.
Figure 9:
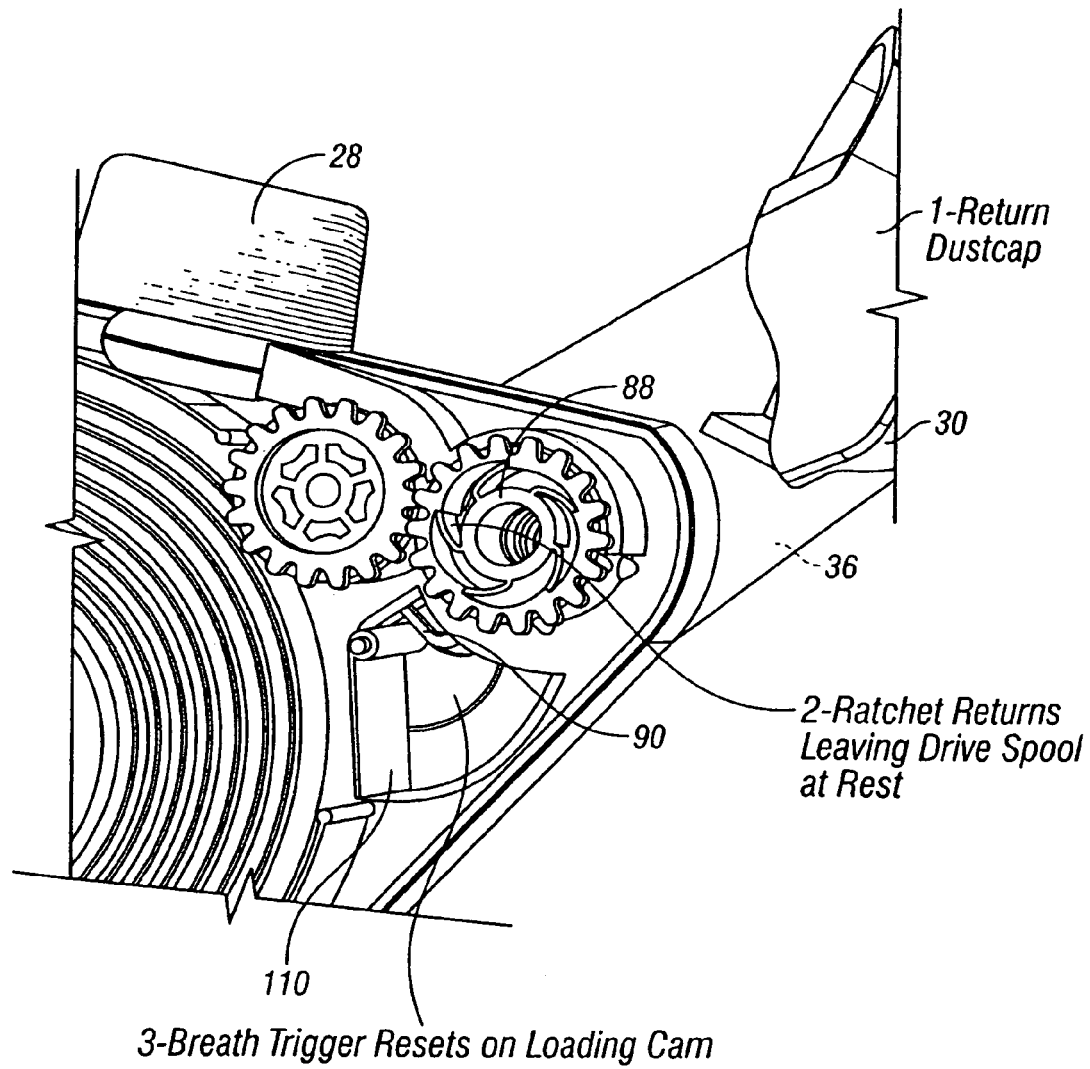
FIG. 9 is a top perspective view thereof showing resetting of the inhaler from the position of FIG. 8 to the initial position shown in FIG. 6.

Turning to FIG. 8, the user places the mouthpiece 28 into the mouth and inhales. Inhalation causes air to flow through the airflow path 50. Specifically, air flows into the housing 22 through the inlet 52 in the housing bottom 26. Air then pushes against the breath wall 112 of the breath flap assembly 110, flows into the chamber inlet duct 46, through the chamber 42 and out into the mouthpiece 28. The air pushing against the breath wall 112 causes the breath flap assembly 110 to pivot, counterclockwise, in FIG. 8. This moves the trigger arm 90 of the ratchet 88 off of the pivot post 116. As the ratchet 88 is now free to move, the torque from the tensioned spring 98 causes the ratchet 88 to rapidly rotate or index approximately 90 degrees. The drive spool 76 moves as well, driven by the ratchet 88. The spur gear 78 on the drive spool 76 correspondingly drives the spur gear 72 on the capstan 70, causing the capstan 70 to turn in the opposite direction by an equal amount of rotation. The tape pins 80 extending through the drive holes 165 in the tear strip 158 pull the dose tape 150 forward. Referring momentarily to FIG. 10A, this drive spool movement pulls the tear strip 158 away from the formpack strip 152. The capstan 70 has recesses 171 around its outer perimeter dimensioned to engage around the blisters 160. Thus, the turning movement of the capstan 70 pulls the formpack layer 152 in a first direction (to the left in FIG. 4) while the drive spool 76 pulls the tear strip 158 in the opposite direction (to the right in FIG. 4). FIG. 10A is a bottom view wherein the directions are reversed.

Referring to FIGS. 10A and 13, as the tear strip 158 is pulled away from the formpack strip 152, the next sequential lidstock disk 168 is sheared out of the lidstock layer 154. This opens the next blister 160, adjacent to the nip or blister opening position 174.

The airflow passing over or past the blister opening position 174 entrains the pharmaceutical powder 162 released from the blister 160. The powder and air flow through the inlet duct 46 into the chamber 42. The air/powder mixture enters the round or toroidal chamber either tangentially or on a chord. The powder/air mixture and beads 44 circulate rapidly within the chamber 42. This movement disperses or aerosolizes the powder 162, and also helps active drug particles separate from excipient or carrier particles in the powder 162, if used.

Referring to FIGS. 4 and 10A, as the tape 150 moves through the tape advance/opening system 58, the tape 150 separates into the used lid strip 170 and the used formpack strip 172. The used lid strip 170, which includes the tear strip 158, adhesive 156 (if used) and the disks 168 sheared out of the lidstock strip 154, is pulled around the drive spool 76, and pushed into the lid material space 66 within the housing 22. The guide 84, shown in FIG. 6, helps to direct the strip 170 into the space 66. Similarly, the used foil strip 172, which includes the formpack strip 152 and the lidstock strip 154 permanently attached to the formpack strip 152 (except for the sheared out lidstock disks 168) moves, with incremental or indexing movement of the capstan 70, into the used formpack strip accumulation space 68. The capstan 70 preferably does not include any tape pins 80, as on the drive spool 76. Rather, the capstan 70 acts as a turning point for the used formpack strip 170. The pulling movement of the drive spool 76 acting on the tape 150 entering the tape advance/opening system 58 pushes the used formpack strip 172 into the space 68.

After inhalation is completed, the inhaler 20 is reset, in preparation for delivering a subsequent dose, by pivoting the dustcap 30 back to its original closed position over the mouthpiece 28, as shown in FIG. 9. This movement turns the ratchet 88 in a second direction, opposite to the first direction (the second direction being counterclockwise in FIG. 9).

The connection between the ratchet 88 and the loading cam 102 allows movement of the dustcap 30 to turn the ratchet 88 only in the second direction i.e., counterclockwise in FIG. 9. The opening movement of the dustcap 30 does not turn the cam 88. As the dustcap 30 is closed, the cam 88 rotates counterclockwise. However, the drive spool 76 does not move, as the ratchet arms 94 on the ratchet 88 flex inwardly and slide over the ratchet teeth 82 on the drive spool 76. Accordingly, during the reset step shown in FIG. 4, as the dustcap 30 is returned to the closed position, the drive spool 76, capstan 70, and tape 150 do not move.

The counterclockwise movement of the ratchet 88 with the closing of the dustcap 30 causes the trigger arm 90 of the ratchet 88 to move back to the position shown in FIG. 6, and simultaneously to reset the breath flap assembly 110 back to the position shown in FIG. 6. The cam recess 104 moves away from the bottom plate 114 of the breath flap assembly 110, preventing movement of the breath flap assembly. The inhaler 20 is then ready to repeat the steps described above to deliver another dose of pharmaceutical powder contained in the next blister 160 approaching the tape advance/opening system 58.

The dose tape 150 may contain up to 120 or more doses. After all doses have been used, the inhaler 20 may be discarded. Alternatively, in a reusable design, the housing 22 may be opened, the used strips 170 and 172 removed and discarded, and a replacement tape 150, in the form of a spool 60, installed.

An advantage of the operation of the inhaler 20, as described above, is that the sealed blister or powder container 160 on the tape 150 is not opened until the user inhales, sufficiently to release the breath flap assembly 110. Accordingly, air is already flowing through the airflow path 50, at the time the powder is released from the blister. This helps to entrain the powder in the airflow. It also prevents inhalation of a stale dose of powder. In addition, since no powder is released until the user inhales on the mouthpiece, the potential for double dosing is greatly reduced, because powder cannot accumulate within the inhaler by opening multiple blisters without inhaling. Unlike breath actuated metered dose inhalers, no propellant gases or canisters are needed, and there is no burst of fast moving compressed gas into the user's mouth.

Another advantage of the inhaler 20 is that the tape pins 80 on the drive spool 76 pull on the tear strip 158 only after the tear strip 158 is separated from the formpack strip 152. This allows high tape moving forces to be applied to the tape 150, without damaging it. As relatively high forces can be used to move the tape 150, and to open blisters as shown in FIG. 13, tape movement and blister opening can be achieved rapidly, so that the powder release occurs at or near the peak of inhalation, when there is rapid airflow through the airflow path 50. Consequently, the inhaler 20 can be breath actuated.

With reference to FIGS. 4 and 5, another advantage is the relatively simple design of the inhaler 20. No clutch or other complicated mechanical components or mechanisms are needed. In addition, the tape 150 has evenly spaced apart blisters 160. As the used tape strips 170 and 172 are not coiled on driving spools, there is no need for compensating drive mechanism movement or clutching. Rather, the movement of the tape advance/opening system 58 is identical for each blister.

As the tear strip 158 is a separate layer or strip (preferably polyester) not involved in sealing the powder, it can be adapted to transfer high forces for movement of the tape 150. This is in contrast to existing tape inhalers which move the tape by acting on the metal foil layers, which are not able to handle high forces as well. Referring to FIGS. 8 and 10A, the drive spool 76 applies force to move the tape 150 not only at the nip or blister opening position 174, but rather over a sector of the drive spool 76 up to or exceeding 90 degrees. This helps to apply advancing and opening forces to the tape 150 rapidly and consistently.

Referring to the sequence of operation steps shown in FIGS. 6, 7, 8, and 9, the dustcap 30 is the only external moving part of the inhaler. Accordingly, to operate the inhaler 20, the user need only move the dustcap between the opened and closed positions. No other manipulation or movement by the user or patient is required. As all other operations within the inhaler 20 are automatic, the human factors of using the inhaler 20 are greatly simplified. Consequently, patient training, and maintaining proper dosing regimen are also simplified.

The blister opening system 58 can of course also be used in other types of inhalers, having varying air flow paths, chambers, and mouthpieces. For example, while the disbursion chamber 40 is generally preferred, it is not an essential element. In addition, while not generally preferred, the blister opening system 58 can be tensioned by a separate lever or other element, independent of the dustcap.

Figure 14:
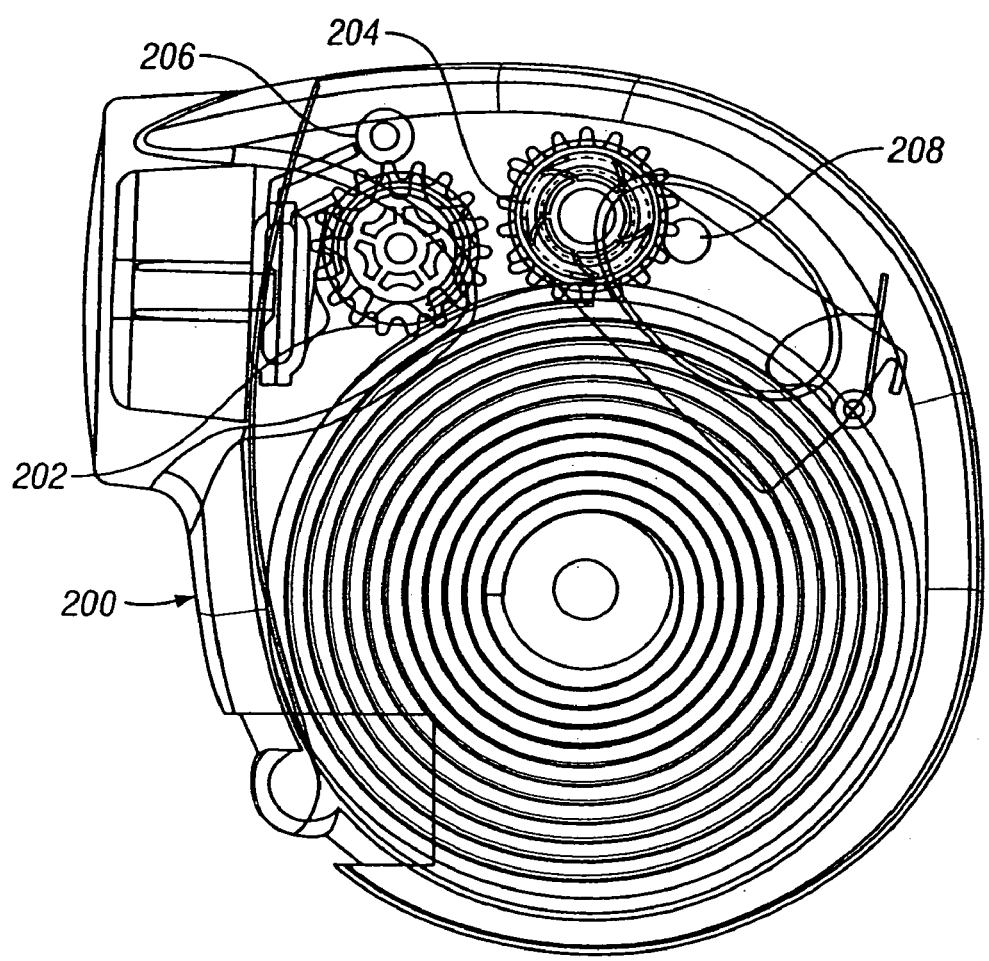
FIG. 14 is a top view of an alternative embodiment.
Figure 15:
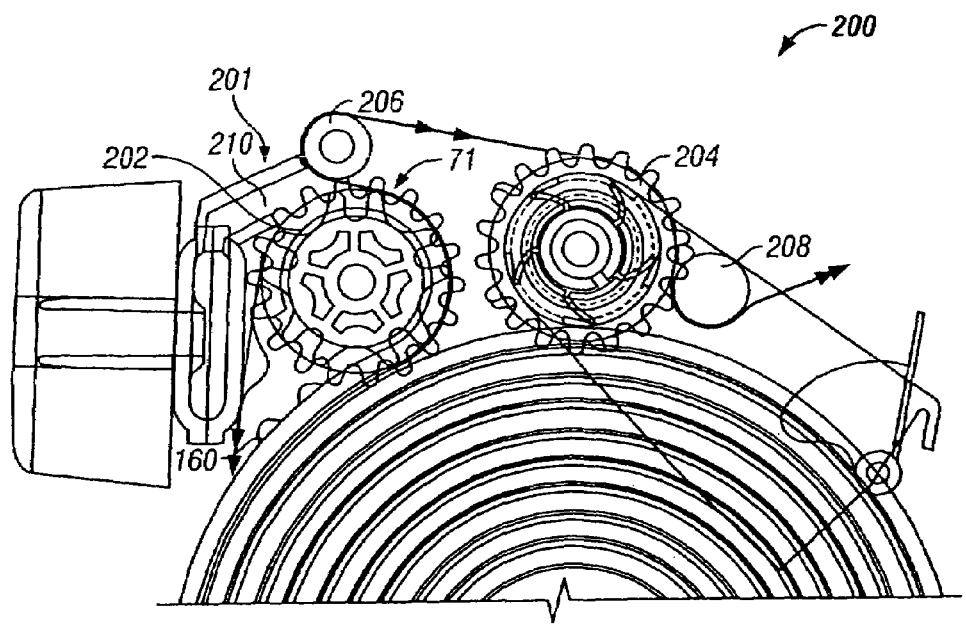
FIG. 15 is an enlarged fragment view of the embodiment shown in FIG. 14.

FIGS. 14 and 15 show a second embodiment 200 having an alternative tape advance/blister opening system 201, similar to the system 58 described above. The alternative tape advance/blister opening system 201 has a capstan 202 having recesses 71 for receiving the blisters, similar to the capstan 70. The system 201 also has a drive spool 204 similar to the drive spool 76. However, the capstan 202 and the drive spool 204 are spaced apart from each other, as shown in FIG. 15. Consequently, they do not directly engage or interact with each other, as in the system 58, and no meshing spur gears are needed. Rather, the tape 150 wraps around the capstan 202, with the blisters facing in, so that they are received or engaged by the recesses 71. The tape 150 separates into a used blister strip 172, which is pushed into the space 68, and a lid strip 170. The lid strip wraps around a capstan idler wheel 206, the drive spool 204, and a drive spool idler wheel 208. The capstan idler wheel 206 reverses the direction of the tape path, and helps to keep the tape engaged with the capstan 202. The drive wheel idler 208 helps to keep the tape 150 wrapped around the drive spool 204. The idler wheels 206 and 208 are free spinning idlers. The air flow path opening into the chamber inlet duct is located between the capstan 202 and the capstan idler wheel 206.

Operation of the tape advance/blister opening system 201 is similar to the system 58, with the following differences. The capstan 202 is driven or turned by the advancing tape. The tape advancing and blister opening force is preferably applied to the tape, in this embodiment, by the drive spool 204 acting on the tear strip 158. As little or no force is applied to the blisters, and because the capstan 202 and the drive spool 204 do not contact each other, potential damage or distortion of the blisters is avoided.

The drive holes 165 in the tape 150 need only be in the tear strip, and not in the formpack layer 152 or the lidstock layer 154. This helps to preserve the integrity of the seal provided by each blister. Water vapor migrates into the blisters over time through the adhesive layer or microscopic gaps between the layers 152 and 154 (rather than through the layers themselves). Consequently, the wider the continuous glue layer, the better the seal or barrier properties of the finished tape. Placing drive holes 165 in the layers 152 and 154 would require that the tape 150 be wider to achieve a given quality or level of sealing. By avoiding drive holes 165 in the layers 152 and 154, the tape 150 and inhaler can be more compact.

Figure 16:
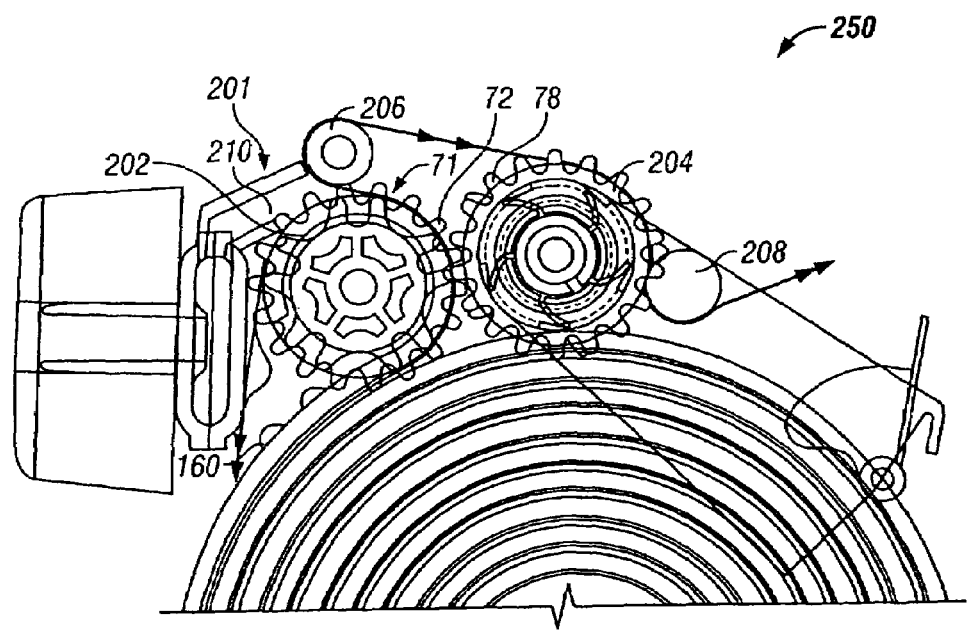
FIG. 16 is an enlarged fragment view of another alternative embodiment.

Referring to FIG. 16, in a similar alternative design 250, gears 72 and 78 are provided on the drive spool 204 and capstan 202, and mesh with each other. However, the capstan 202 and drive spool 204 may still be spaced apart sufficiently to avoid damage or distortion of the blisters as the blisters approach the opening position.

Thus, a novel dose tape and inhaler have been shown and described. Various changes and substitutions may of course be made, without departing from the spirit and scope of the invention. The invention, therefore, should not be limited, except to the following claims and their equivalents.

What is claimed is:

1. A method for operating a dry powder inhaler, providing a dry powder inhaler, said dry powder inhaler comprising a dose tape having spaced apart doses of a powder pharmaceutical, each dose being in a respective sealed blister, said inhaler comprising a blister opening system which sequentially opens a blister on the tape, said blister opening system being breath actuated, the method comprising the steps of:
   routing the dose tape between first and second rotating elements;
   spring biasing the first rotating element to turn in a first direction;
   holding the first rotating element from rotating, against the spring biasing; and
   releasing the first rotating element, and allowing it to rotate a fraction of one rotation, when air flows adjacent to the first rotating element.

2. The method of claim 1 wherein the first rotating element comprises a ratchet.

3. The method of claim 2 wherein the first rotating element comprises a drive spool engaged by the ratchet.

4. The method of claim 1 wherein the second rotating element comprises a capstan.

5. The method of claim 1 further comprising the step of tensioning the spring by moving a dustcap on the inhaler.

6. The method of claim 1 further comprising the step of separating an area of a second layer of a dose tape from a first layer of the dose tape with rotating movement of the first rotating element.

7. A method for operating a dry powder inhaler, providing a dry powder inhaler, said dry powder inhaler comprising a dose tape having spaced apart doses of a powder pharmaceutical, each dose being in a respective sealed blister, said inhaler comprising a blister opening system which sequentially opens a blister on the tape, said blister opening system being breath actuated, the method comprising the steps of:
routing the dose tape between first and second rotating elements;
spring biasing the first rotating element to turn in a first direction;
holding the first rotating element from rotating against the spring biasing; and
triggering the release of the first rotating element by inhaling through the inhaler.

8. The method of claim 7, wherein the step of triggering the release of the first rotating element by inhaling through the inhaler causes air to flow adjacent to the first rotating element.

9. The method of claim 7, wherein the step of triggering the release of the first rotating element by inhaling through the inhaler causes the first rotating element to rotate only a fraction of one rotation.

10. The method of claim 7, wherein the first rotating element comprises a drive spool engaged by a ratchet.

11. The method of claim 10, wherein the second rotating element comprises a capstan.

12. The method of claim 7, further comprising the step of tensioning the spring by moving a dustcap on the inhaler.

13. The method of claim 7, further comprising the step of separating an area of a second layer of a dose tape from a first layer of the dose tape by rotating the first rotating element.

14. A method for operating a dry powder inhaler, comprising the steps of:
providing the dry powder inhaler, which comprises a dose tape having spaced apart doses of a powder pharmaceutical, each dose being in a separately sealed blister, the inhaler comprising a blister opening mechanism for sequentially opening each sealed blister on the tape, wherein the blister opening mechanism is breath actuated;
routing the dose tape between first and second rotating elements;
spring biasing the first rotating element to turn in a first direction;
holding the first rotating element from rotating against the spring biasing; and
actuating the blister opening mechanism and triggering the release of the first rotating element by inhaling through the inhaler.

* * * * *